(12) United States Patent
Neilson et al.

(10) Patent No.: US 6,544,740 B1
(45) Date of Patent: Apr. 8, 2003

(54) TREATMENT OF ENDOMETRIOSIS WITH ANTILEUKOPROTEASE

(75) Inventors: Lorna I. Neilson, Vista, CA (US); Zhen Li, Mission Viejo, CA (US)

(73) Assignee: Reprogen, Inc., Irvine, CA (US)

( * ) Notice: Subject to any disclaimer, the term of this patent is extended or adjusted under 35 U.S.C. 154(b) by 21 days.

(21) Appl. No.: 09/605,134

(22) Filed: Jun. 27, 2000

Related U.S. Application Data

(60) Provisional application No. 60/142,157, filed on Jul. 1, 1999.

(51) Int. Cl.$^7$ .............................. C12Q 1/68; C12P 21/06
(52) U.S. Cl. ........................................ 435/6; 435/69.1
(58) Field of Search .................... 435/69.1, 6

(56) References Cited

U.S. PATENT DOCUMENTS

| 4,845,076 A | 7/1989 | Heinzel et al. |
| 5,843,673 A | * 12/1998 | Sharpe-Timms ............ 435/7.1 |
| 5,871,956 A | 2/1999 | Bandyopadhyay et al. |
| 5,900,400 A | 5/1999 | Thompson et al. |

FOREIGN PATENT DOCUMENTS

WO    WO97/03694    2/1997

OTHER PUBLICATIONS

Simmen et al. Regulation of synthesis of uterine secretory proteins: Evidence for differential induction of porcine uteroferrin and antileukoproteinase gene expression. Biology of Reproduction, vol. 44, pp. 191–200, 1991.*
Reed et al. Porcine endometrial glandular epithelial cells in vitro: transcriptional activities of the pregnancy–associated genes encoding antileukoproteinase and uteroferrin, Biol Reprod., vol. 55(2): 469–477, 1996.*
Sharpe–Timms, Kathy L. Basic research in endometriosis. Obstet Gynecol Clin North Am. 24(2): 269–90, 1997.*
Badinga, et al. "Pregnancy–Associated Endometrial Expression of Antileukoproteinase Gene is Correlated With Epitheliochorial Placentation," Molecular Reproduction and Development, 38:357–363 (1994).
Banda, et al. "Elastin Degradation," Methods Enzymol, 144:288–305 (1987).
Bieth et al. "The Synthesis and Analytical Use of a Highly Sensitive Convenient Substrate of Elastase," Biochemical Medicine, 11, 350–357 (1974).
Bischof, et al. "Involvement of trophoblast in embryo implantation: regulation by paracrine factors," J. Reprod. Immunol 39:167 (1998).
Bischof, et al. "Metalloproteinases, cell adhesion and invasion molecules in human implantation and placentation," Elsevier Science B.V., 651–659 (1998).
Boyle, et al. "Doxycycline inhibits elastin degradation and reduces metalloproteinase activity in a model of aneurysmal disease," J Vasc Surg. 2:354–61 (1998).

Bruner et al. "Suppression of matrix metalloproteinases inhibits establishment of ectopic lesions by human endometrium in nude mice," Clin Invest. 99(12):2851–7 (1997).
Casslen, et al. "Localization and quantitation of a low molecular weight proteinase inhibitor, antileukoprotease, in the human uterus," Hoppe Seylers Z Physiol Chem. 362(7):953–61 (1981).
Coffman, et al. "Trout ovulatory proteins are partially responsible for the anti–proteolytic activity found in trout coelomic fluid," Biol Reprod. 59(3):497–502 (Sep. 1998).
Eisenberg, et al. "Location of the Protease–inhibitory Region of Secretory Leukocyte Protease Inhibitor," The Journal of Biological Chemistry, 265 (14) 7976–7981 (1990).
Farmer, et al. "Complementary DNA cloning and regulation of expression of the messenger RNA encoding a pregnancy–associated porcine uterine protein related to human antileukoproteinase," Mol Endocrinol. 4(8):1095–104 (1990).
Giudice, et al. "Status of current research on endometriosis," J Reprod Med. 43(3 Suppl):252–62. (1998).
Goel, et al. "Role of proteases in tumor invasion and metastasis," Indian J Exp Biol. 35(6):553–64 (1997).
Heinzel, et al. "Molecular cloning and expression of cDNA for human antileukoprotease from cervix uterus," Eur J Biochem. 160(1):61–7 (1986).
Hiemstra, et al. "Antibacterial Activity of Antileukoprotease," Infection and Immunity 4520–4524 (1996).
Ikeda, et al. "Anti–invasive activity of synthetic serine protease inhibitors and its combined effect with a matrix metalloproteinase inhibitor," Anticancer Res. 18(6A):4259–65 (1998).
Kramps, et al. "Role of antileukoprotease in the human lung," Ann N Y Acad Sci. 624:97–108 (1991).
Kramps, et al. "Localization of low molecular weight protease inhibitor in serous secretory cells of the respiratory tract," J. Histochem Cytochem 29:712 (1980).
Lee et al. "A serine elastase inhibitor reduces inflammation and fibrosis and preserves cardiac function after experimentally–induced murine myocarditis," Nat Med. 4(12):1383–91 (1998).
Lu et al. "Endometriosis: current management," Mayo Clin Proc 70:453–63 (1995).

(List continued on next page.)

Primary Examiner—Jeffrey Fredman
Assistant Examiner—Suryaprabha Chunduru
(74) Attorney, Agent, or Firm—Townsend and Townsend and Crew LLP

(57) ABSTRACT

This invention provides methods for diagnosing and treating endometriosis, and promoting implantation of an embryo. The methods involve determining or modulating antileukoprotease activity in a subject.

7 Claims, 2 Drawing Sheets

OTHER PUBLICATIONS

Marchand, et al. "The elastase–induced expression of secretory leukocyte protease inhibitor is decreased in remodeled airway epithelium," Eur J Pharmacol. 336:187–96 (1997).

McElvaney, et al. "Modulation of airway inflammation in cystic fibrosis. In vivo suppression of interleukin–8 levels on the respiratory epithelial surface by aerolization of recombinant secretory leukoprotease inhibitor," J Clin Invest. 90(4):1296–301 (1992).

Nagase, et al. "Activation Mechanisms of Matrix Metalloproteinases," Biol. Chem., 378, 151–160 (1997).

Nagase, et al. "Stepwise Activation mechanisms of the Precursor of Matrix Metalloproteinase 3 (Stromelysin) by Proteinases and (4–Aminophenyl) mercuric Acetate," Biochemistry 29, 5783–5789 (1990).

Ohlsson, et al. "Secretory leukocyte protease inhibitor in the male genital tract: PSA–induced proteolytic processing in human semen and tissue localization," J. Androl 16:64 (1995).

Osteen et al. "Steroid and growth factor regulation of matrix metalloproteinase expression and endometriosis," Semin. Reprod Endocrinol 14 (3):247–255 (1996).

Rabbani, Shafaat Ahmed. "Metalloproteases and urokinase in angiogenesis and tumor progression," In Vivo, 12:135–42 (1998).

Reed, et al. "Porcine endometrial glandular epithelial cells in vitro: transcriptional activities of the pregnancy–associated genes encoding antileukoproteinase and uteroferrin," Biol Reprod. 55(2):469–77 (1996).

Rudolphus, et al. "Detection of extracellular neutrophil elastase in hamster lungs after intratracheal instillation of *E. coli* lipopolysaccharide using a fluorogenic, elastase–specific, synthetic substrate," Am J Pathol. 141(1):153–60 (1992).

Rudolphus, et al. "Inhibition of lipopolysaccharide–induced pulmonary emphysema by intratracheally instilled recombinant secretory leukocyte proteinase inhibitor," Am Rev Respir Dis. 147(2):442–7 (1993).

Schnebli, et al. "Recombinant elastase inhibitors for therapy," Ann N Y Acad Sci. 624:212–8 (1991).

Seemuller, et al. "The acid–stable proteinase inhibitor of human mucous secretions (HUSI–I), antileukoprotease). Complete amino acid sequence as revealed by protein and cDNA sequencing and structural homology to whey proteins and Red Sea turtle proteinase inhibitor," FEBS Lett 199(1):43 (1986).

Sharpe–Timms, Kathy L. "Basic research in endometriosis," Obstet Gynecol Clin North Am. 24(2):269–90 (1997).

Shi, et al. "Molecular cloning and expression of human alveolar macrophage cathespin S, an elastinolytic cysteine protease," J Biol Chem. 267(11):7258–62 (1992).

Sillem, et al. "Ectopic growth of endometrium depends on its structural integrity and proteolytic activity in the cynomolgus monkey (*Macaca fascicularis*) model of endometriosis," Fertil Steril. 66(3):468–73 (1996).

Simmen et al. "Ontogeny, immunocytochemical localization, and biochemical properties of the pregnancy–associated uterine elastase/cathespin–G protease inhibitor, antileukoproteinase (ALP): monospecific antibodies to a synthetic peptide recognize native ALP," Endocrinology. 130(4):1957–65 (1992).

Simmen, et al. "Regulation of synthesis of uterine secretory proteins: evidence for differential induction of porcine uteroferrin and antileukoproteinase gene expression," Biol Reprod. 44(1):191–200 (1991).

Spuijbrock et al. "Early endometriosis invades the extracellular matrix," Fertil. Steril 58(5):929–933 (1992).

Takahashi, et al. "Regulation of matrix metalloproteinase–9 and inhibition of tumor invasion by the membrane–anchored glycoprotein RECK," Proc Natl Acad Sci U S A. 95(22):13221–6 (1998).

Tegner et al. "Isolation and partial characterization of a low molecular weight acid stable protease inhibitor from human bronchial secretion," Physiol Chem 358:431 (1977).

Thompson, et al. "Isolation, properties, and complete amino acid sequence of human secretory leukocyte protease inhibitor, a potent inhibitor of leukocyte elastase," Proc Natl Acad Sci U.S.A. 83(18):6692–6 (1986).

Todorovich–Hunter, et al. "Increased pulmonary artery elastolytic activity in adult rats with monocrotaline–induced progressive hypertensive pulmonary vascular disease compared with infant rats with nonprogressive disease," Am Rev Respir Dis. 146(1):213–23 (1992).

Tomee, et al. "Secretory leukoprotease inhibitor: a native antimicrobial protein presenting a new therapeutic option?" Thorax. 53(2):114–6 (1998).

Tyagi, et al. "Extracellular matrix regulation of metalloproteinase and antiproteinase in human heart fibroblast cells," J Cell Physiol. 167(1):137–47 (1996).

Van–Seuningen, et al. "Separation of the two domains of human mucus proteinase inhibitor: inhibitory activity is only located in the carboxyl–terminal domain," Biochem Biophys Res Commun.179(3):1587–92 (1991).

Werb, et al. "Extracellular matrix remodeling during morphogenesis," Ann N Y Acad Sci. 857:110–8 (1998).

Westin, et al. "IgE–mediated histamine release from nasal mucosa is inhibited by SLPI (secretory leukocyte protease inhibitor) to the level of spontaneous release," Mediators Inflamm. 7(3):217–20 (1998).

Wiedow, et al. "Antileukoprotease in human skin: an antibiotic peptide constitutively produced by keratinocytes," Biochem Biophys Res Commun. 248(3):904–9 (1999).

Willems, et al. "Antileucoprotease in the developing fetal lung," Thorax. 43(10):784–6 (1988).

Ying, et al. "Functions of the N–terminal domain of secretory leukoprotease inhibitor," Biochemistry. 33(18):5445–50 (1994).

Zhang, et al. "Secretory leukocyte protease inhibitor suppresses the production of monocyte prostaglandin H synthase–2, prostaglandin E2, and matrix metalloproteinases," J Clin Invest. 99(5):894–900 (1997).

Bergqvist et al. "A comparison of cathespin D levels in endometriotic tissue and in uterine endometrium," Fertility and Sterility 65:1130–1134 (1996).

Panyutich et al. "human neutrophil defensin and serapins form complexes and inactivate each other," American Journal of Respiratory Cell and Molecular Biology 12:351–357 (1995).

Reed et al. "Control of secretory leukocyte protease inhibitor gene expression in the porcine periimplantation endometrium: a case of maternal–embryo communication," Biology of Reproduction 58:448–457 (1998).

Ronnberg "Endometriosis and infertility," Annals of Medicine 22:91–96 (1990).

Sillem et al. "Extracellular matrix remodeling in the endometrium and its possible relevance to the pathogenesis of endometriosis," Human Reproductive Update 4:730–735 (1998).

Suzumori et al. "Expression of secretory leukocyte protease inhibitor in women with endometriosis," Fertility and Sterility 72:857–867 (1999).

* cited by examiner

FIG. 1A

```
Cys Leu Asp Pro Val Asp Thr Pro Asn Pro Thr Arg Arg Lys Pro
TGCCTGGATCCTGTTGACACCCCAAACCCAACCAAGGAGGAAGCCT       316
ACGGACCTAGGACAACTGTGGGGTTTGGGTTGTTCCTCCTTCGGA

Gly Lys Cys Pro Val Thr Tyr Gly Gln Cys Leu Met Leu Asn Pro
GGGAAGTGCCCAGTGACTTATGGCCAATGTTTGATGCTTAACCCC         361
CCCTTCACGGGTCACTGAATACCGGTTACAAACTACGAATTGGGG

Pro Asn Phe Cys Glu Met Asp Gly Gln Cys Lys Arg Asp Leu Lys
CCCAATTTCTGTGAGATGGATGGCCAGTGCAAGCGTGACTTGAAG         406
GGGTTAAAGACACTCTACCTACCGGTCACGTTCGCACTGAACTTC

Cys Cys Met Gly Met Cys Gly Lys Ser Cys Val Ser Pro Val Lys
TGTTGCATGGCATGTGTGGGAAATCCTGCGTTTCCCCTGTGAAA        451
ACAACGTACCCGTACACACCCTTTAGGACGCAAAGGGGACACTTT

Ala Stop
GCTTGATTCCTGCCATATGGAGGAGGCTCTGGAGTCCTGCTCTGT        496
CGAACTAAGGACGGTATACCTCCTCCGAGACCTCAGGACGAGACA GTGGTCCAGGTCCTTTCCACCCTGAGACTTGGCTCCACCCCC         541
CACCAGGTCCAGGAAAGGTGGACTCTGAACCGAGGTGGGGGG

CCCCCCCCCCCCCCCCCCCTGCAG
GGGGGGGGGGGGGGGGGGGACGTC
```

FIG. 1B

TREATMENT OF ENDOMETRIOSIS WITH ANTILEUKOPROTEASE

CROSS-REFERENCES TO RELATED APPLICATIONS

This application claims the benefit of provisional application No. 60/142,157, filed Jul. 1, 1999.

STATEMENT AS TO RIGHTS TO INVENTIONS MADE UNDER FEDERALLY SPONSORED RESEARCH AND DEVELOPMENT

Not applicable.

BACKGROUND OF THE INVENTION

This invention relates to the field of medical treatment and diagnosis. More particularly, it relates to the diagnosis and treatment of endometriosis and infertility.

Endometriosis is a gynecologic disorder estimated to occur in 10% of reproductive age women. The disease occurs in up to 50% of infertile females (L. C. Gudice et al., *J. Reprod. Med.*, 43:252 (1998)). Endometriosis is defined clinically as the presence of lesions within the peritoneal cavity. Usually, endometriosis is confined to the pelvic and lower abdominal cavity; however, it has been reported in other areas, including the pleural cavity. These lesions originate from endometrial tissue normally found within the interior lining of the uterus. It is believed that cells from the uterine lining (endometrium) are released via the fallopian tubes into the abdominal cavity through retrograde menstruation. While the precise mechanisms by which the displaced endometrial tissue forms ectopic lesions remain to be elucidated, the initial establishment of this disease is clearly an invasive event.

Current diagnosis of endometriosis usually involves laparoscopy, a surgical procedure, or magnetic resonance imaging, a costly procedure. No markers have been approved for a non-invasive diagnosis. Surgical therapies involve removal or ablation of ectopic lesions and often hysterectomy. Non-surgical therapies involve systemic administration of hormones and hormone antagonists (e.g. gonadotropin-releasing hormone (GnRH) agonists) or progestins (e.g., danazol), which can be accompanied by serious side effects, and can only be administered for a limited time period (P. Y. Lu and S. J. Ory, *Mayo Clin. Proc.*, 70:453 (1995)). Contemporary surgical and non-surgical therapies suffer from significant morbidity and lack of long term efficacy. Therefore, there is an enormous unmet need for the development of non-invasive diagnostics and new pharmacological approaches for the treatment of endometriosis.

Antileukoprotease (ALP) is a low molecular weight protein (~14 kd). It is also known as secretory leukoprotease inhibitor (SLPI) (Y. Zhang et al., *J. Clinical Invest.*, 99:894 (1997)) and as $\alpha_1$-proteinase inhibitor ($\alpha_1$-PI) (J. A. Kramps et al., *Ann. New York Acad. Sci.*, 624:97 (1991)). The major substrates of antileukoprotease, in vivo, are elastase and cathepsin G, enzymes which degrade collagen and other components of the extracellular matrix. It is conventionally thought that ALP plays an important role in the defense of epithelial surfaces against proteolytic damage (R. C. Thompson et al., *Proc. Natl. Acad. Sci. USA*, 83:6692; J. A. Kramps et al., *J. Histochem. Cytochem.* 29:712 (1986); K. Ohlsson et al., *J. Androl.*, 16:64 (1995)).

ALP has been localized in the human cervix (R. Heinzel et al., *Eur. J. Biochem.*, 160:61(1986)) and the fetal and adult human lung (L. N. Willems et al., *Thorax*, 43:784 (1988); J. A. Kramps et al., *J. Histochem. Cytochem.* 29:712 (1981)). ALP has also been purified from the parotid and submandibular glands, saliva, tears and gut (H. Tegner and O. K. Olsson, *Hoppe Seylers Z. Physiol. Chem.*, 358:431 (1977); U. A. Seemuller et al., *FEBS Lett.*, 199(1):43 (1986)) and the porcine endometrium (S. J. Farmer et al., *Mol Endocrinol*, 4(8):1095–104 (1995)). It is reported to inhibit release of IgE-mediated histamine from nasal mucosa. U. Westin et al. *Mediators of Inflammation*, 7:217 (1998).

Antileukoprotease is not expressed in non-pregnant human endometrial tissue. B. Casslen et al., *Hoppe-Seyler's Z. Physiol. Chem.*, 362:953 (1981). However, ALP is expressed in pregnant pig endometrium. K. L. Reed, *Biology of Reproduction*, 55:469 (1996) and L. Badinga et al, *Molec. Repro. and Dev.*, 38:357 (1994). The expression of ALP in the endometrium is regulated by estrogen and progesterone but these hormones do not effect its expression in the lung. S. J. Farmer et al. (1990) *Molec. Endocrino.l* 4(8):1095–104. R. C. Simmen et al. (1991) *Biol. Reprod.* 44(1):191–200. Local application of recombinant ALP has been used to treat cystic fibrosis and pulmonary emphysema. A. S. Rudolphus et al. (1993) *Am. Rev. Respir. Dis.* 147(2):442–7. N. G. McElvaney (1992) *J. Clin. Invest.* 90(4): 1296–301.

Nucleic acids encoding antileukoprotease are described in U.S. Pat. No. 5,845,076 (R. Heinzel et al.). Active analogs of antileukoprotease are described in U.S. Pat. No. 5,871,956 (P. K. Bandyopadhyay et al.) and U.S. Pat. No. 5,900,400 (R. C. Thompson et al.). Antileukoprotease has 107 amino acids. Its structure includes two domains. The C-terminal domain has the protease inhibitory activity. S. P. Eisenberg et al., *J. Biol. Chem.*, 265:7976 (1990) and I. Van-Seuningen et al., *Biochem. Biophys. Res. Comm.*, 179:1587(1991).

Extracellular matrix (ECM) degradation by secreted proteases is essential for endometrial functions such as blastocyst implantation and menstruation. M. D. Spuijbroek et al. (1992) *Fertil. Steril.* 58(5):929–33 showed a basement membrane and ECM degradation product, namely the N-terminal propeptide of type III collagen, to be increased in the peritoneal fluid (PF) of patients with early (subtle) forms of endometriosis which points toward an increased activity of extracellular matrix degrading proteases in this condition. The expression of matrix metalloproteinases (MMPs) MMP-3, MMP-7 and tissue inhibitor of metalloproteinase-1 (TIMP-1) have also been documented in lesions of endometriosis. K. G. Osteen et al. *Semin. Reprod. Endocrinol.*, 14(3):247–55 (1996).

While the precise mechanisms by which displaced endometrial tissue leads to ectopic lesions remain speculative, the initial establishment of this disease is clearly an invasive event requiring the breakdown of the extracellular matrix. Extensive literature supports the role of proteases in the invasive behavior of normal and neoplastic cells.

M. Sillem et al., *Fertility and Sterility* 66:468 (1996) reported that enzymatic digestion of endometrial fragments and treatment with a proteinase inhibitor, aprotinin, impaired ectopic growth. MMP's are a family of 12 structurally homologous enzymes having an atom of zinc in their active domain. They are secreted as inactive enzymes and activated upon proteolysis. Y. Zhang et al., *J. Clinical Invest.*, 99:894 (1997) reported that antileukoprotease inhibited production by cultured monocytes of prostaglandin H synthase-2, which was accompanied by a decrease in production of $PGE_2$, resulting in suppression of matrix metalloproteinases MMP-1, a collagenase, and MMP-9, a gelatinase. K. L. Bruner et al., *Metalloproteinases and Experimental Endometriosis,* 99:2851 (1997) reported that steroidal suppression of matrix metalloproteinases MMP-3, a stromelysin, and MMP-7, a matrilysin, in human endometrial tissue inhibited establishment of ectopic lesions by the tissue in nude mice. Matrix metalloproteinases also have been implicated in promoting the invasive behavior of cytotrophoblast cells into the uterine endometrium. P. Bischof et al., *J. Reprod. Immunol.* 39:167 (1998)

SUMMARY OF THE INVENTION

We have discovered that antileukoprotease (ALP) is differentially expressed (over-expressed by about 20-fold) in eutopic endometrial tissue of endometriosis patients compared with ectopic tissue in such patients. We used a 10,000 gene oligonucleotide array to compare gene expression in eutopic and ectopic endometrium from patients with endometriosis. This study resulted in a catalog of 1,988 genes that are differentially expressed between eutopic and ectopic endometrium. There were 726 genes expressed at higher levels in the ectopic endometriotic lesions when compared to the eutopic endometrium and 1,262 genes expressed at higher levels in the eutopic endometrium when compared to ectopic lesions. Of these genes, antileukoprotease, a serine protease inhibitor, was expressed 25 times less in ectopic lesions than in the eutopic endometrium from endometriosis patients. It is believed that the action of elastase and cathepsin G contributes to endometriosis by promoting the invasion of ectopic endometrial tissue into tissue in the peritoneal cavity. Accordingly, this invention provides methods for diagnosing endometriosis by detecting elevated levels of ALP in eutopic endometrium, and methods of treating endometriosis by providing a mammalian subject with an amount of ALP effective to inhibit ectopic implantation of endometrial fragments. In one embodiment, this amount is an amount effective to inhibit the activity of elastase and cathepsin G in the peritoneum.

In one aspect this invention provides a method for the treatment of endometriosis in a subject comprising administering to the subject an amount of antileukoprotease effective to inhibit the activity of elastase or cathepsin G, thereby inhibiting ectopic implantation of endometrial fragments.

In another aspect this invention provides a method comprising measuring an amount of antileukoprotease activity in an endometrial tissue sample from a subject.

In another aspect this invention provides a method for diagnosing endometriosis comprising: a) measuring a test amount of antileukoprotease activity in a eutopic endometrial tissue sample from a subject, and b)comparing the test amount with a normal amount of antileukoprotease activity; whereby a test amount above the normal amount provides a positive sign in a diagnosis of endometriosis.

In another aspect this invention provides a method for diagnosing endometriosis comprising: a) measuring a test amount of antileukoprotease activity in an ectopic endometrial tissue sample from a subject, and b) comparing the test amount with a normal amount of antileukoprotease activity; whereby a test amount below the normal amount provides a positive sign in a diagnosis of endometriosis.

In another aspect this invention provides a method for diagnosing endometriosis comprising: a) measuring a first test amount of antileukoprotease activity in an ectopic endometrial tissue sample from a subject, b) measuring a second test amount of antileukoprotease activity in a eutopic endometrial tissue sample from a subject, and c) determining a test difference between the first test amount and the second test amount; d) comparing the test difference with a normal difference between amounts of antileukoprotease activity in ectopic and eutopic endometrial tissue; whereby a test difference greater than a normal difference provides a positive sign in a diagnosis of endometriosis.

In another aspect this invention provides a method for identifying a modulator of antileukoprotease activity comprising: a) contacting a test compound which is not an elastase or cathepsin G modulator with antileukoprotease; b) measuring an amount of antileukoprotease activity; and c) determining whether the measured amount is different than a control amount of activity when antileukoprotease is not contacted with the agent; whereby a measured amount different than a control amount identifies the compound as a modulator of antileukoprotease.

BRIEF DESCRIPTION OF THE DRAWINGS

FIGS. 1*a* and 1*b* show a DNA sequence (SEQ ID NO:1) and a deduced amino acid sequence (SEQ ID NO:2) of antileukoprotease. Taken from U.S. Pat. No. 4,845,076 (Heinzel et al.).

DETAILED DESCRIPTION OF THE INVENTION

I. DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991).

"Nucleic acid" refers to a polymer composed of nucleotide units (ribonucleotides, deoxyribonucleotides, related naturally occurring structural variants, and synthetic non-naturally occurring analogs thereof) linked via phosphodiester bonds, or other synthetic linkages. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a nucleic acid, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. An amplified or assembled recombinant nucleic acid may be included in a suitable vector, and the vector can be used to transform a suitable host cell. A host cell that comprises the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

"Expression control sequence" refers to a nucleotide sequence in a nucleic acid that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression cassette" refers to a recombinant nucleic acid construct comprising an expression control sequence operatively linked to an expressible nucleotide sequence. "Expression vector" refers to a vector comprising an expression cassette. Expression vectors include all those known in the art, such as cosmids, plasmids (e.g., naked or contained in liposomes) and viruses that incorporate the recombinant nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Allelic variant" refers to any of two or more polymorphic forms of a gene occupying the same genetic locus. Allelic variations arise naturally through mutation, and may result in phenotypic polymorphism within populations. Gene mutations can be silent (no change in the encoded polypeptide) or may encode polypeptides having altered amino acid sequences. "Allelic variants" also refer to cDNAs derived from mRNA transcripts of genetic allelic variants, as well as the proteins encoded by them.

Two proteins are "homologs" of each other if they exist in different species, are derived from a common genetic ancestor and share at least 70% amino acid sequence identity.

"Conservatively modified variant" refers to a polypeptide in which one or more amino acids has been substituted with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

A polypeptide has an amino acid sequence that is "substantially identical" to the amino acid sequence of antileukoprotease if it has an amino acid sequence at least 80%, at least 90%, at least 95%, at least 98% or at least 99% identical over the length of the shorter sequence.

A polypeptide is an active analog of antileukoprotease if it has a sequence that is substantially identical to that of antileukoprotease (SEQ ID NO:2) and if it has activity to inhibit elastase or cathepsin G activity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387–395 (1984).

Another example of algorithms that are suitable for determining percent sequence identity and sequence similarity are the BLAST and the BLAST 2.0 algorithm, which are described in Altschul et al., *J. Mol. Biol.* 215:403–410 (1990) and Altschul et al., *Nucleic Acids Res.* 25:3389–3402 (1977)). Software for performing BLAST analyses is publicly available through the National Center for Biotechnology Information (http://www.ncbi.nlm.nih.gov/). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915 (1989)).

"Stringent hybridization conditions" refers to 50% formamide, 5×SSC and 1% SDS incubated at 42° C. or 5×SSC and 1% SDS incubated at 65° C., with a wash in 0.2×SSC and 0.1% SDS at 65° C.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, dioxigenin, or haptens and proteins for which antisera or monoclonal antibodies are available.

"Linker" refers to a molecule that joins two other molecules, either covalently, or through ionic, van der Walls or hydrogen bonds, e.g., a nucleic acid molecule that hybridizes to one complementary sequence at the 5' end and to another complementary sequence at the 3' end, thus joining two non-complementary sequences.

"Pharmaceutical composition" refers to a composition suitable for pharmaceutical use in a subject. A pharmaceutical composition comprises a pharmacologically effective amount of an active agent and a pharmaceutically acceptable carrier. "Pharmacologically effective amount" refers to that amount of an agent effective to produce the intended pharmacological result, e.g., inhibit activity of cathepsin G or elastase, or implantation of ectopic endometrial tissue. "Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in REMINGTON'S PHARMACEUTICAL SCIENCES, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). Preferred pharmaceutical carriers depend upon the intended mode of administration of the active agent. A "pharmaceutically acceptable salt" is a salt that can be formulated into a compound for pharmaceutical use including, e.g., metal salts (sodium, potassium, magnesium, calcium, etc.) and salts of ammonia or organic amines.

A "subject" of diagnosis or treatment is a human or non-human mammal.

"Treatment" refers to prophylactic treatment or therapeutic treatment.

A "prophylactic" treatment is a treatment administered to a subject who does not exhibit signs of a disease or exhibits only early signs for the purpose of decreasing the risk of developing pathology.

A "therapeutic" treatment is a treatment administered to a subject who exhibits signs of pathology for the purpose of diminishing or eliminating those signs.

"Diagnostic" means identifying the presence or nature of a pathologic condition. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis.

"Test amount" refers to an amount of an analyte in a subject sample, which is then compared to a normal amount of the analyte in a sample (e.g., from a healthy individual) such that the relative comparison of the values provides a reference value for diagnosing a designated disease. Depending upon the method of detection, the test amount may be a determination of the amount of the analyte, but it is not necessarily an amount. The test amount may also be a relative value, such as a plus or a minus score, and also includes an amount indicating the presence or absence of the analyte in a sample.

"Normal amount" refers to an amount or a range of an analyte in a biological sample that indicates health or lack of pathology.

"Diagnostic amount" refers to an amount of an analyte in a subject sample that is consistent with a particular diagnosis for a designated disease.

"Prognostic amount" refers to an amount or range of an analyte in a subject sample that is consistent with a particular prognosis for a designated disease.

"Small organic molecule" refers to organic molecules of a size comparable to those organic molecules generally used in pharmaceuticals. The term excludes organic biopolymers (e.g., proteins, nucleic acids, etc.). Preferred small organic molecules range in size up to about 5000 Da, up to about 2000 Da, or up to about 1000 Da.

"Bioorganic molecule" refers to an organic molecule typically found in living systems, e.g. nucleic acids, proteins, carbohydrates, lipids, steroids, etc.

"Chemical library" refers to a collection of compounds of different structures. Generally, the compounds will fall into the same class of chemical compounds, e.g., DNA, polypeptides, benzodiazepines, small organic molecules, etc. Libraries of compounds can be divided into two main classes. A first class is libraries of polymers. A second class is libraries of functionalized scaffold molecules. In either case, the various chemical linkages that can be created with the methods of this invention are at the discretion of the practitioner.

II. ANTILEUKOPROTEASE

A. Protein

"Antileukoprotease" or "ALP" refers to a protein having the sequence of SEQ ID NO:2 ("full-length ALP") and active analogs of it that inhibit the activity of elastase or cathepsin G. Active analogs include "C-terminal domain fragments" of ALP. One example of a C-terminal domain fragment of ALP is a fragment comprising amino acids 55–107 of ALP (SEQ ID NO:2). Active analogs also include "substituted versions" of ALP whose amino acid sequence differs from that of ALP by the inclusion of amino acid substitutions. Such analogs are described in U.S. Pat. No. 5,871,956 (P. K. Bandyopadhyay et al.) and U.S. Pat. No. 5,900,400 (R. C. Thompson et al.). ALP useful in this invention also includes allelic variants. Mammalian homologs can be used, but are not preferred because they can provoke an immunogenic response. Generally, active analogs of ALP can be identified as having amino acid sequences substantially identical to the ALP of SEQ ID NO:2. Nucleic acids encoding active analogs will hybridize under stringent conditions to the ALP nucleotide sequence of SEQ ID NO:1.

ALP can be obtained by PCR of cDNA of human cervix uterus cells using primers based on the nucleotide sequence of SEQ ID NO:1.

B. Pharmaceutical Compositions

Antileukoprotease can be formulated as a pharmaceutical composition for delivery in a variety of ways. Typical routes of administration include both enteral and parenteral. These include, without limitation, subcutaneous, intramuscular, intravenous, intraperitoneal, intramedullary, intrapericardial, intrabursal, intravaginal, oral, sublingual, ocular, nasal, topical, transdermal, transmucosal, intravaginal or anal. The mode of administration can be, e.g., via swallowing, inhalation, injection or topical application to a surface (e.g., eyes, mucus membrane, skin). Particular formulations typically are appropriate for specific modes of administration. Various contemplated formulations include, for example, aqueous solutions, solid formulations, aerosol formulations and transdermal formulations.

Examples of aqueous solutions include, for example, water, saline, phosphate buffered saline, Hank's solution, Ringer's solution, dextrose/saline, glucose solutions and the like. The compositions can contain pharmaceutically acceptable auxiliary substances as required to approximate physiological conditions or to improve stability, appearance or ease of administration, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration.

Aqueous solutions are appropriate for injection and, in particular, for intravenous injection. Intravenous injection is a particularly appropriate means of delivery for using the compound as a hypnotic agent. The intravenous solution can include detergents and emulsifiers such as lipids. Aqueous solutions also are useful for enteral administration as tonics and administration to mucous or other membranes as, e.g., nose or eye drops. The composition can contain the compound in an amount of about 1 mg/ml to 100 mg/ml, more preferably about 10 mg/ml.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be through nasal sprays, for example, or using suppositories.

For topical administration, the agents are formulated into ointments, creams, salves, powders and gels. In one embodiment, the transdermal delivery agent can be DMSO. Transdermal delivery systems can include, e.g., patches.

For inhalation, the compound is preferably administered in the form of an aerosol, liquid or solid. For aerosol administration, the compound preferably is supplied in finely divided form along with a surfactant and propellant. A surfactant may be required if the agent is immiscible in the propellant.

The surfactant preferably is soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides, can be employed. The surfactant can constitute 0.1%–20% by weight of the composition, preferably 0.25%–5%.

The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above can also be employed. In producing the aerosol, a container equipped with a suitable valve is filled with the appropriate propellant, containing the agent as a solution or as finely divided particles and surfactant. The ingredients are thus maintained at an elevated pressure until released by action of the valve.

A nebulizer or aerosolizer device for administering compounds typically delivers a dose of about concentration of between about 1 and 50 mg per inhalation.

In preparing pharmaceutical compositions of the present invention, it can be desirable to modify the complexes of the present invention to alter their pharmacokinetics and biodistribution. For a general discussion of pharmacokinetics, See, REMINGTON'S PHARMACEUTICAL SCIENCES, supra, Chapters 37–39. A number of methods for altering pharmacokinetics and biodistribution are known to one of ordinary skill in the art. Examples of such methods include protection of the complexes in vesicles composed of substances such as proteins, lipids (for example, liposomes), carbohydrates, or synthetic polymers.

Single or multiple administrations of the compositions can be carried out with dose levels and pattern being selected by the treating physician. In any event, the pharmaceutical formulations should pro-vide a quantity of a compound sufficient to treat the patient effectively.

The total effective amount of a compound of the present invention can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a compound of the present invention required to obtain an effective dose in a subject depends on many factors including the age and general health of the subject, the route of administration, the number of treatments to be administered and the judgment of the prescribing physician. In view of these factors, the skilled artisan would adjust the dose so as to provide an effective dose for a particular use.

C. Cellular Transfection and Gene Therapy

ALP also can be delivered by gene therapy methods. These methods involve providing target cells with expression vectors comprising expression control sequences active in the cell operatively linked with a nucleotide sequence encoding the ALP.

The present invention provides transfecting cells in vitro and in vivo with nucleic acids encoding ALP polypeptides. These nucleic acids can be inserted into any of a number of well known vectors for the transfection and transformation of target cells and organisms as described below. The nucleic acids are transfected into cells, ex vivo or in vivo, through the interaction of the vector and the target cell. The gene encoding the ALP polypeptide, under the control of a promoter, expresses the ALP polypeptide, which is then secreted, thereby inhibiting serine proteases. Much of the product remains cell-associated upon secretion, and therefore provides advantages over direct administration of an ALP polypeptide.

For a review of gene therapy procedures, see Anderson, Science (1992) 256:808–813; Nabel and Felgner (1993) TIBTECH 11: 211–217; Mitani and Caskey (1993) TIBTECH 11: 162–166; Mulligan (1993) Science 926–932; Dillon (1993) TIBTECH 11: 167–175; Miller (1992) Nature 357: 455–460; Van Brunt (1988) Biotechnology 6(10): 1149–1154; Vigne (1995) Restorative Neurology and Neuroscience 8: 35–36; Kremer and Perricaudet (1995) British Medical Bulletin 51(1) 31–44; Haddada et al. (1995) in Current Topics in Microbiology and Immunology Doerfler and Böhm (eds) Springer-Verlag, Heidelberg Germany; and Yu et al., Gene Therapy (1994) 1:13–26.

Delivery of the gene or genetic material into the cell is the first critical step in gene therapy treatment. A large number of delivery methods are well known to those of skill in the art. Such methods include, for example liposome-based gene delivery (Debs and Zhu (1993) WO 93/24640; Mannino and Gould-Fogerite (1988) BioTechniques 6(7): 682–691; Rose U.S. Pat No. 5,279,833; Brigham (1991) WO 91/06309; and Felgner et al. (1987) Proc. Natl. Acad. Sci. USA 84: 7413–7414), and replication-defective retroviral vectors harboring a therapeutic nucleic acid sequence as part of the retroviral genome (see, e.g., Miller et al. (1990) Mol. Cell. Biol. 10:4239 (1990); Kolberg (1992) J. NIH Res. 4:43, and Cornetta et al. Hum. Gene Ther. 2:215 (1991)). Widely used retroviral vectors include those based upon Moloney murine leukemia virus (MMuLV), gibbon ape leukemia virus (GaLV), simian immunodeficiency virus (SIV), human immunodeficiency virus (HIV), and combinations thereof. See, e.g., Buchscher et al. (1992) J. Virol. 66(5) 2731–2739; Johann et al. (1992)J. Virol. 66 (5):1635–1640 (1992); Sommerfelt et al. (1990) Virol. 176:58–59; Wilson et al. (1989)J. Virol. 63:2374–2378; Miller et al., J. Virol. 65:2220–2224 (1991); Wong-Staal et al., PCT/US94/05700, and Rosenburg and Fauci (1993) in Fundamental Immunology, Third Edition Paul (ed) Raven Press, Ltd., New York and the references therein, and Yu et al., Gene Therapy (1994) supra).

Adenoviral vectors are also commonly used for introduction of nucleic acids into mammals. See, e.g., Berns et al. (1995) Ann. NY Acad. Sci. 772: 95–104; Ali et al. (1994) Gene Ther. 1: 367–384; and Haddada et al. (1995) Curr. Top. Microbiol. Immunol. 199 (Pt 3): 297–306 for review.

Adeno-associated virus (AAV)-based vectors are also used to transduce cells with target nucleic acids, e.g., in the in vitro production of nucleic acids and peptides, and in in vivo and ex vivo gene therapy procedures. See, West et al. (1987) Virology 160:38–47; Carter et al. (1989) U.S. Pat. No. 4,797,368; Carter et al. WO 93/24641 (1993); Kotin (1994) Human Gene Therapy 5:793–801; Muzyczka (1994) J. Clin. Invest. 94:1351 and Samulski (supra) for an overview of AAV vectors. Construction of recombinant AAV vectors are described in a number of publications, including Lebkowski, U.S. Pat. No. 5,173,414; Tratschin et al. (1985) Mol. Cell. Biol. 5(11):3251–3260; Tratschin, et al. (1984) Mol. Cell. Biol., 4:2072–2081; Hermonat and Muzyczka (1984) Proc. Natl. Acad. Sci. USA, 81:6466–6470; McLaughlin et al. (1988) and Samulski et al. (1989)J. Virol., 63:03822–3828. Cell lines that can be transformed by rAAV include those described in Lebkowski et al. (1988) Mol. Cell. Biol., 8:3988–3996.

In one embodiment, "naked" DNA and/or RNA encoding an ALP polypeptide is introduced directly into a tissue. See, e.g., U.S. Pat. No. 5,580,859. Other methods such as "biolistic" or particle-mediated transformation (see, e.g., Sanford et al., U.S. Pat. Nos. 4,945,050; 5,036,006) are also suitable for introduction of ALP activity into cells of a mammal according to the invention. These methods are useful not only for in vivo introduction of DNA into a mammal, but also for ex vivo modification of cells for reintroduction into a mammal. As for other methods of delivering nucleic acids encoding polypeptides having ALP activity, if necessary, DNA administration is repeated in order to maintain the desired level of activity.

Vectors (e.g., retroviruses, adenoviruses, liposomes, etc.) containing therapeutic nucleic acids can be administered directly to the organism for transduction of cells in vivo. Administration is typically by intravenous administration to deliver the ALP nucleic acid to vascular endothelial cells. Administration by intraperitoneal injection is also suitable, as are other routes normally used for introducing a molecule into ultimate contact with blood or tissue cells. The packaged nucleic acids are administered in any suitable manner, preferably with pharmaceutically acceptable carriers. Suitable methods of administering such packaged nucleic acids are available and well known to those of skill in the art, and, although more than one route can be used to administer a particular composition, a particular route can of ten provide a more immediate and more effective reaction than another route.

The particles can be delivered in by any appropriate mode and in any appropriate pharmaceutical composition, including injection in an aqueous solution or liposome, or aerosol formulations (e.g., they can be "nebulized") to be administered via inhalation.

In determining the effective amount of the vector to be administered in the treatment or prophylaxis of endometriosis, the physician evaluates vector toxicities, progression of the disease, and the production of anti-vector antibodies, if any. In general, the dose equivalent of a naked nucleic acid from a vector is from about 1 μg to 1 mg for a typical 70 kilogram patient, and doses of vectors used to deliver the nucleic acid are calculated to yield an equivalent amount of therapeutic nucleic acid.

III. TREATMENT OF ENDOMETRIOSIS

Antileukoprotease is under-expressed in ectopic endometrial tissue compared with eutopic endometrial tissue in endometriosis patients. It is believed that this underexpression results in increased activity of elastase and cathepsin G produced by neutrophils. This increased activity, in turn, results in increased rates of implantation of ectopic endometrial tissue into the peritoneum. Accordingly, this invention provides a method of treating endometriosis by administering an effective amount of antileukoprotease to a subject. In one embodiment, the effective amount is an amount effective to inhibit the activity of elastase and cathepsin G. The amount administered can be between 1 μg and 1000 mg, between 10 μg and 100 mg or between 100 μg and 10 mg. ALP can be delivered in several administrations over the course of several days or weeks.

Antileukoprotease can be administered either prophylactically, in a person at risk of developing endometriosis, or therapeutically, to a person diagnosed with endometriosis. Antileukoprotease can be delivered as a pharmaceutical composition, or can be delivered via gene therapy. In the case of a pharmaceutical composition, antileukoprotease is preferably delivered either intravaginally or intraperitoneally. Intravaginal administration can be, e.g., via a suppository. Intraperitoneal administration can be, e.g., via injection in an appropriate carrier.

IV. DIAGNOSIS AND STAGING OF ENDOMETRIOSIS

Antileukoprotease is a marker for endometriosis. In endometriosis patients, it is over-expressed in eutopic endometrial tissue compared with ectopic tissue. Therefore, measuring antileukoprotease amounts or activity in endometrial tissue is useful in diagnosing and staging the disease. Accordingly, this invention provides methods that involve detecting and quantifying antileukoprotease in endometrial tissue.

One diagnostic method involves determining a test amount of antileukoprotease in eutopic endometrial tissue of a subject, and comparing that amount to a normal or diagnostic amount or range of antileukoprotease. A test amount above a normal amount or range and in the diagnostic amount or range is a positive sign in the diagnosis of endometriosis. This sign can be used alone or, preferably, in combination with other signs in making a final diagnosis of endometriosis. Furthermore, it is expected that the particular amount measured is useful in staging the disease, different stages exhibiting different amounts and eutopic/ectopic ratios.

Another method useful in the diagnosis of endometriosis involves determining a test amount of antileukoprotease in ectopic endometrial tissue of a subject, and comparing that amount to a normal or diagnostic amount or range of antileukoprotease. A test amount below the normal amount or range and in the diagnostic amount or range is a positive sign in the diagnosis of endometriosis. This sign also can be used alone or, preferably, in combination with other signs in making a final diagnosis of endometriosis.

Because antileukoprotease is over-expressed in eutopic endometrium compared with ectopic endometrial tissue, comparing the amount of antileukoprotease in ectopic and eutopic tissue is useful in the diagnosis of endometriosis and its staging. A ratio of antileukoprotease between eutopic and ectopic tissue that is diagnostic of endometriosis is above 2, more preferably above 15, most preferably above 20.

Figure 1A:
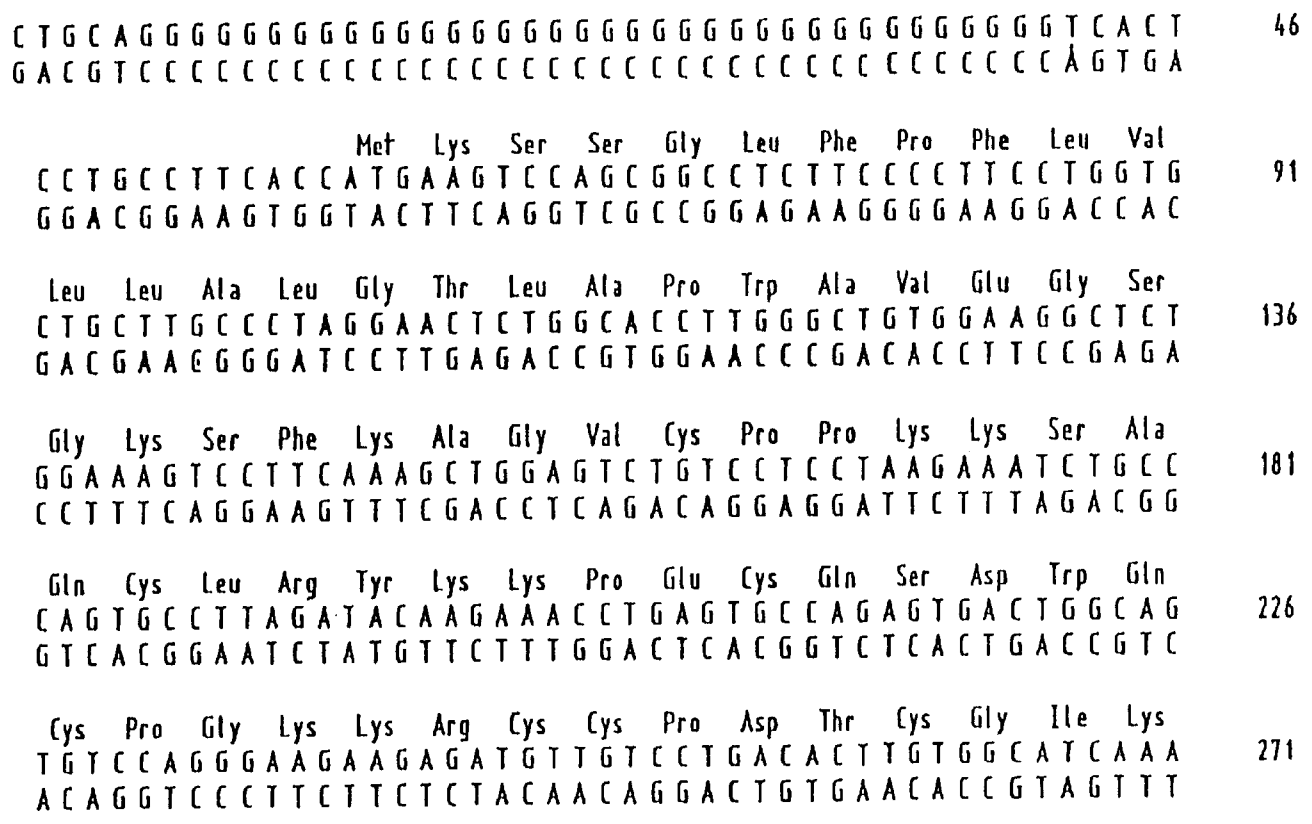

One method of measuring the amount of antileukoprotease is by measuring the amount of antileukoprotease mRNA in the tissue. Many methods are known for quantifying mRNA. These include, for example, real-time PCR, northern blot and RNase protection. In one method, mRNA is immobilized to a solid support and detected using a detectably labeled nucleic acid probe. Probes can comprise sequences complementary to any part of the antileukoprotease sequence, as shown in FIG. 1. The amount of labeled probe bound is quantitated with usual methods. Before immobilization, the mRNA can be separated from other mRNA's, for example by gel electrophoresis, or a portion of it can be amplified using, e.g., PCR. In another method, the mRNA is labeled and hybridized to an oligonucleotide array containing probes specific for antileukoprotease. Commercially available sources that provide such arrays include Affymetrix, Inc. (Santa Clara, Calif., USA), Hyseq (Sunnyvale, Calif., USA), Incyte Pharmaceuticals (Palo Alto, Calif., USA) and Nanogen (San Diego, Calif., USA). In another method, mRNA can be detected by mass spectrometry. In such methods, the mRNA can be specifically captured on a mass spec probe and captured detected by desorption in the mass spectrometer. See, for example, International patent publication WO 98/59361 (Hutchens and Yip) and U.S. Pat. No. 5,605,798 (Koster).

Another method of measuring the amount of antileukoprotease is by measuring the amount of antileukoprotease activity. An antileukoprotease activity assay is described below.

V. TREATMENT OF INFERTILITY

One cause of lack of fertility involves unsuccessful implantation of the trophoblast into the uterine wall. This action, in turn, involves the activity of proteases that model the tissue of the wall. The over-activity of antileukoprotease can inhibit the activity of elastase and cathepsin G, and can inhibit production of various metalloproteinases. Accordingly, this invention provides a method of improving fertility by administering an amount of an antileukoprotease inhibitor effective to promote implantation of the embryo into the endometrium. In one embodiment, the effective amount is an amount effective to inhibit activity of elastase or cathepsin G. Antileukoprotease inhibitors can be identified by the screening techniques discussed herein.

The inhibitors should be administered before fertilization or during early pregnancy (e.g., before time for implantation). Inhibitors can be administered by any suitable route and in any suitable carrier. Preferably, they are administered intravaginally.

VI. SCREENING FOR MODULATORS OF ANTILEUKOPROTEASE ACTIVITY

This invention also provides screening methods involving contacting antileukoprotease with a test agent that does not modulate the activity of elastase or cathepsin G, and determining whether the agent modulates the activity of antileukoprotease. Test agents that modulate antileukoprotease activity are candidates for use in the methods of this invention.

Test agents that do not modulate the activity of elastase or cathepsin G can be identified in a direct elastase or cathepsin G assay. Elastase assays are well known in the art. Elastase is commercially available from Sigma. One elastase assay is described by M. J. Banda et al., *Meth. in Enz.*, 144:288 (1987). Natural (e.g., pancreatic) or recombinant elastase, is incubated with a labeled elastin substrate for several hours. After incubation, the insoluble material is removed. Label that is released as a result of elastin degradation by elastase is then detected in the supernatant.

In a newer assay, a soluble elastase substrate, Suc-(Ala)$_3$-nitroalanine, is incubated with elastase. Activity of elastase is detected by the release of p-nitroalanine, detected by absorbance at 410 nm. J. Blieth et al., *Biochemical Medicine*, 11:350 (1974). Standard curves and controls are provided as usual for quantitation.

Cathepsin G assays also are known in the art. They also involve contacting cathepsin G with a test agent and a substrate and determining activity as a function of activity on the substrate. Cathepsin G is commercially available from Sigma. Succinyl-alanyl-analyl-prolyl-phenlanaline-p-nitroanilide can be used as a substrate of cathepsin G. See, e.g., O. Weidow et al., *Biochem. Biophys. Res. Comm.*, 248:904 (1998).

An assay for determining activity of antileukoprotease involves, in certain embodiments, employing antileukoprotease as a "test agent" in an elastase or cathepsin G activity assay. In this assay, antileukoprotease activity is registered as an inhibition of elastase or cathepsin G activity. Thus, inhibition of antileukoprotease results in increased activity of elastase or cathepsin G, and potentiation of antileukoprotease activity results in decreased activity of elastase or cathepsin G.

Methods of screening test agents for their ability to modulate antileukoprotease activity involve contacting a compound that is not an elastase or cathepsin G modulator with antileukoprotease, and determining whether the compound modulates antileukoprotease activity. The step of determining whether the compound modulates ALP activity can involve performing an ALP assay as described herein for elastase or cathepsin G. The compound can, for example, be pre-incubated with ALP, or it can be provided to a mixture that contains ALP, elastase and a substrate of elastase or, alternatively, cathepsin G and a substrate of cathepsin G. The test compound also is added to the mixture to determine its effect on the activity of antileukoprotease. Compounds that modulate the activity of ALP are recorded.

Assays for modulators of biological activity generally involve administering a test agent to an assay system, and determining whether the agent alters the amount of the biological activity in the assay system. This determination generally involves measuring the amount of biological activity of the assay system resulting after administration of the test agent, and comparing that amount to a control or standard amount of biological activity. The control amount preferably reflects the biological activity of the assay system when no agent has been added. For example, the determination can involve performing a side-by-side comparison of biological activity with and without administration of the test compound. In another method, the practitioner can create a "standard curve" in which the system is exposed to varying amounts of the agent and the amount of biological activity is measured. The activity measurements are extrapolated to a "zero amount" of agent administration. In this way the amount of activity upon administration of the compound can be compared to the amount of activity when no agent is administered. The practitioner also can compare the amount of biological activity resulting from the administration of different amounts of the test agent. In this case one amount provides a "test" level of activity and the other amount provides a "control" level of activity. A difference between the test amount and the control amount indicates that the agent modulates biological activity. The comparison between test amounts of activity and control amounts can provide a simple "yes" or "no" answer to the question of whether the agent modulates activity. Alternatively, if the answer is "yes" that amount can be quantified. Modulation includes both up-regulation and down-regulation of activity.

This invention contemplates the testing of any chemical or biological agent in the activity assay. Thus, the "agent" can be a chemical compound (e.g., a small organic molecule or a bioorganic molecule), a mixture of chemical compounds, or an extract made from biological materials such as bacteria, plants, fungi, or animal cells or tissues. The system of this invention is useful for testing libraries of compounds by exposing different cultures of the recombinant bacteria to different agents in the library.

The agent to be tested can be selected from a number of sources. For example, combinatorial libraries of molecules are available for screening. Using such libraries, tens of thousands of molecules can be screened for regulatory activity. In one preferred embodiment, high throughput screening methods involve providing a library containing a large number of test agents. Such "combinatorial chemical libraries" are then screened in one or more assays to identify those library members (particular chemical species or subclasses) that display a desired characteristic activity. The compounds thus identified can serve as conventional "lead compounds" or can themselves be used as potential or actual therapeutics. Preparation and screening of combinatorial chemical libraries is well known to those of skill in the art.

The present invention provides novel materials and methods for treating and diagnosing endometriosis. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document Applicants do not admit that any particular reference is "prior art" to their invention.

What is claimed is:

1. A method of measuring an amount of antileukoprotease in an endometrial tissue sample from a human subject comprising measuring an amount of antileukoprotease mRNA in the endometrial tissue sample from the subject, wherein the amount of antileukoprotease in the sample is measured as a function of antileukoprotease mRNA in the sample.

2. The method of claim 1 wherein the endometrial tissue is eutopic endometrial tissue.

3. The method of claim 1 wherein the endometrial tissue is ectopic endometrial tissue.

4. A method for diagnosing endometriosis comprising:
a) measuring a test amount of antileukoprotease mRNA in a eutopic endometrial tissue sample from a subject, and
b) comparing the test amount with a normal amount of antileukoprotease mRNA;
whereby a test amount above the normal amount provides a positive sign in a diagnosis of endometriosis.

5. A method for diagnosing endometriosis comprising:
a) measuring a test amount of antileukoprotease mRNA in an ectopic endometrial tissue sample from a subject, and
b) comparing the test amount with a normal amount of antileukoprotease mRNA;
whereby a test amount below the normal amount provides a positive sign in a diagnosis of endometriosis.

6. A method for diagnosing endometriosis comprising:
a) measuring a first test amount of antileukoprotease mRNA in an ectopic endometrial tissue sample from a subject, b) measuring a second test amount of antileukoprotease mRNA in a eutopic endometrial tissue sample from a subject, and c) determining a test ratio of the first test amount to the second test amount;

d) comparing the test ratio with a normal ratio of amounts of antileukoprotease mRNA in ectopic to eutopic endometrial tissue;

whereby a test ratio greater than a normal ratio provides a positive sign in a diagnosis of endometriosis.

7. A method for diagnosing endometriosis comprising:

a) measuring a first test amount of antileukoprotease mRNA in an ectopic endometrial tissue sample from a subject, b) measuring a second test amount of antileukoprotease mRNA in a eutopic endometrial tissue sample from a subject, and c) determining a test ratio of the first test amount to the second test amount;

d) comparing the test ratio with a normal ratio of amounts of antileukoprotease mRNA in ectopic to eutopic endometrial tissue;

whereby a test ratio greater than a normal ratio provides a positive sign in a diagnosis of endometriosis, and wherein the normal ratio is fifteen to one.

\* \* \* \* \*